(12) United States Patent
Haraya et al.

(10) Patent No.: US 10,603,262 B2
(45) Date of Patent: Mar. 31, 2020

(54) COSMETIC COMPOSITION FOR USE ON HAIR AND CONTAINING AN ACYL BASIC AMINO ACID DERIVATIVE

(71) Applicant: AJINOMOTO CO., INC., Tokyo (JP)

(72) Inventors: Nana Haraya, Kawasaki (JP); Shun Kobayashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/631,515

(22) Filed: Jun. 23, 2017

(65) Prior Publication Data

US 2017/0281494 A1 Oct. 5, 2017

Related U.S. Application Data

(63) Continuation of application No. PCT/JP2015/086214, filed on Dec. 25, 2015.

(30) Foreign Application Priority Data

Dec. 25, 2014 (JP) .................................. 2014-262711

(51) Int. Cl.
| | | |
|---|---|---|
| *A61K 8/42* | (2006.01) | |
| *A61K 8/44* | (2006.01) | |
| *A61Q 5/12* | (2006.01) | |
| *A61Q 5/02* | (2006.01) | |
| *A61Q 5/00* | (2006.01) | |
| *A61K 8/41* | (2006.01) | |

(52) U.S. Cl.
CPC .............. *A61K 8/42* (2013.01); *A61K 8/416* (2013.01); *A61K 8/44* (2013.01); *A61Q 5/00* (2013.01); *A61Q 5/02* (2013.01); *A61Q 5/12* (2013.01); *A61K 2800/5426* (2013.01)

(58) Field of Classification Search
None
See application file for complete search history.

(56) References Cited

U.S. PATENT DOCUMENTS

| | | | |
|---|---|---|---|
| 4,640,943 A | 2/1987 | Meguro et al. | |
| 6,410,005 B1 * | 6/2002 | Galleguillos | ............ A61K 8/90 424/45 |
| 6,555,708 B1 | 4/2003 | Yamato et al. | |
| 6,921,747 B2 * | 7/2005 | Hanabusa | ................. C09D 5/04 514/18.8 |
| 2003/0103921 A1 * | 6/2003 | Brucks | ................. A61K 8/0295 424/66 |
| 2004/0248812 A1 * | 12/2004 | Hanabusa | ................. C09D 5/04 514/18.8 |
| 2009/0042846 A1 * | 2/2009 | Gupta | ...................... A61K 8/63 514/173 |
| 2011/0177019 A1 * | 7/2011 | Dickinson | ............... A61K 8/042 424/70.15 |
| 2014/0350128 A1 | 11/2014 | Hanabusa et al. | |

FOREIGN PATENT DOCUMENTS

| | | |
|---|---|---|
| EP | 0 336 265 A2 | 10/1989 |
| EP | 1 473 027 A1 | 11/2004 |
| JP | 60-67406 A | 4/1985 |
| JP | 61-137812 A | 6/1986 |
| JP | 1-242517 A | 9/1989 |
| JP | 3-74312 A | 3/1991 |
| JP | 2003-105221 A | 4/2003 |
| JP | 2004-323505 A | 11/2004 |
| JP | 2010-184905 A | 8/2010 |
| WO | WO 01/014317 A1 | 3/2001 |
| WO | WO 2013/118896 A1 | 8/2013 |
| WO | WO 2004/189014 A1 | 11/2014 |

OTHER PUBLICATIONS

Liang et al. Journal of Surfactants and Detergents 2014 17:693-701 available online Dec. 7, 2013 (Year: 2014).*
International Search Report dated Mar. 22, 2016 in PCT/JP2015/086210.
Masahiro Suzuki, et al., "L-Lysine Based Gemini Organogelators: their Organogelation Properties and Thermally Stable Organogels" Org. Biomol. Chem., 2003, 1, pp. 4124-4131.
Masahiro Suzuki, et al., "Novel Dumbbell-Form Low-Molecular-Weight Gelators Based on L-Lysine: their Hydrogelation and Organogelation Properties" New Journal of Chemistry, 2005, 29, pp. 1439-1444.
Extended European Search Report dated May 15, 2018 in Patent Application No. 15873265.1, citing documents AO and AP therein, 9 pages.

* cited by examiner

*Primary Examiner* — Robert A Wax
*Assistant Examiner* — Caralynne E Helm
(74) *Attorney, Agent, or Firm* — Oblon, McClelland, Maier & Neustadt, L.L.P.

(57) ABSTRACT

The present invention provides a composition containing component (A): a compound represented by the formula (1)

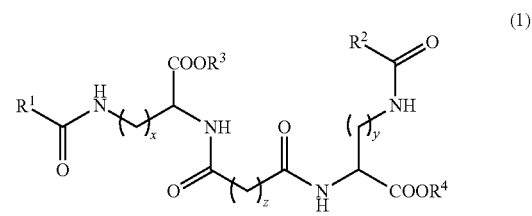

wherein each symbol is as described in the DESCRIPTION, or a salt thereof and component (B): a cationic surfactant, which is superior in the usability during rinsing, which makes the hair surface after treatment smooth and free of dry feeling, provides a uniform touch feeling from the root of the hair to the tip thereof, and can be utilized as an aqueous cosmetic.

16 Claims, No Drawings

COSMETIC COMPOSITION FOR USE ON HAIR AND CONTAINING AN ACYL BASIC AMINO ACID DERIVATIVE

CROSS REFERENCES TO RELATED APPLICATIONS

This application is a continuation of International Patent Application No. PCT/JP2015/086214, filed on Dec. 25, 2015, and claims priority to Japanese Patent Application No. 2014-262711, filed on Dec. 25, 2014, all of which are incorporated herein by reference in their entireties.

BACKGROUND OF THE INVENTION

Field of the Invention

The present invention relates to a composition containing (A): an acyl basic amino acid derivative, and (B): a cationic surfactant, which is used as, for example, a cosmetic for hair.

Discussion of the Background

Repeated chemical treatments and heat treatments on the hair cause accumulation of damage particularly at hair tips. Accordingly, there is a problem that the touch feeling is different between the root with a small degree of damage and hair tips with a great damage. Therefore, a hair cosmetic that makes hair tips closer to those of healthy hair and provides a uniform touch feeling from the root of the hair to the tip thereof is desired.

N-long chain acyl lysine is used for cosmetics and the like since it shows properties of good slipperiness and good spreadability on hair, less irritation to the skin, good attachability to the skin, reduction of "greasiness" and "stickiness" derived from oil agent and moisturizer and the like (patent documents 1-4 etc.). A hair cosmetic containing N-long chain acyl lysine and a surfactant has been reported to have an antistatic effect and an effect superior in combing property (patent document 5).

On the other hand, it has been reported that the hair treated with a cosmetic containing $N^\varepsilon$-lauroyllysine as N-long chain acyl lysine, diester as a dibasic acid, and a cationic surfactant is inferior in uniform smoothness and slip feeling (patent document 6). Moreover, N-long chain acyl lysine has problems in that 1) it is poorly soluble in water and oil, which limits its use to a solid (powder), 2) since it has high water-repellency, affinity to water is poor, which in turn causes difficulty in being stably blended in an aqueous cosmetic, 3) since it coagulates in the obtained aqueous cosmetic, the cosmetic loses smoothness, and 4) friction radically increases when it is contacted with an oil agent component in cosmetics, and frictional feeling becomes strong (patent documents 3, 7 etc.).

It has been reported that a compound represented by the following formula:

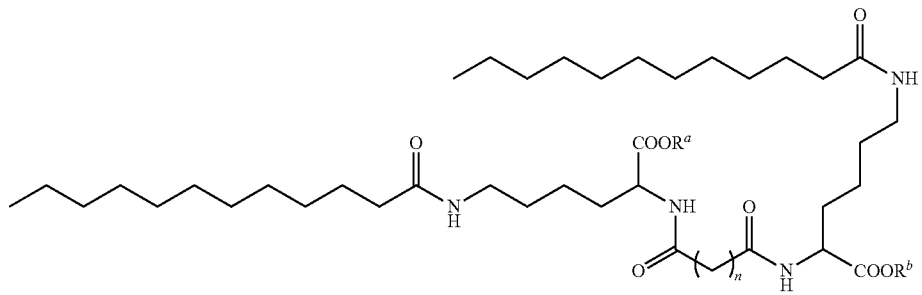

wherein $R^a$ and $R^b$ are each a hydrogen atom or an alkyl group, and n is an integer of 0 to 12, or a salt thereof (hereinafter to be also referred to as "lauroyl amino acid derivative") is useful for gelation or solidifying water and a liquid organic medium (patent document 8, non-patent document 1 and non-patent document 2 etc.).

However, a hair composition containing a lauroyl amino acid derivative and cationic surfactant, and a cosmetic containing the composition have not been reported heretofore.

DOCUMENT LIST

Patent Documents patent document 1: WO 01/014317
patent document 2: JP-A-61-137812
patent document 3: JP-A-60-67406
patent document 4: JP-A-3-74312
patent document 5: JP-A-1-242517
patent document 6: JP-A-2010-184905
patent document 7: JP-A-2003-105221
patent document 8: JP-A-2004-323505

Non-Patent Document non-patent document 1: Org. Biomol. Chem., 2003, 1, 4124-4131
non-patent document 2: New J. Chem., 2005, 29, 1439-1444

SUMMARY OF THE INVENTION

Problems to be Solved by the Invention

An object of the present invention is to provide a composition superior in usability during rinsing, which makes hair surface after treatment smooth and free of dry feeling, provides a uniform touch feeling from the root of the hair to the tip thereof, and can be utilized as an aqueous cosmetic.

Means of Solving the Problems

The present inventors have conducted intensive studies in an attempt to achieve the above-mentioned object and found that a composition containing component (A): a compound represented by the following formula (1) (hereinafter sometimes to be also referred to as "compound (1)") or a salt thereof, and component (B): a cationic surfactant can be utilized as an aqueous cosmetic, is free of sliminess during rinsing, can be rinsed off soon, and that the hair surface after a treatment with the above-mentioned composition is smooth and without a dry feeling, and the composition provides a uniform touch feeling from the root of the hair to the tip thereof and is superior gathering of hair tips, which resulted in the completion of the present invention.

Therefore, the present invention provides the following.

[1] A composition comprising component (A): a compound represented by the formula (1)

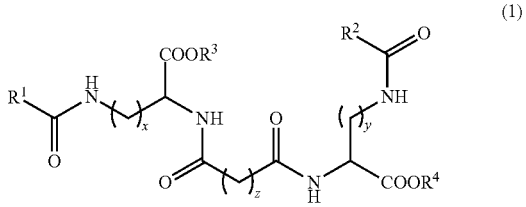

wherein
$R^1$ and $R^2$ are each independently an alkyl group having 5-21 carbon atoms or an alkenyl group having 5-21 carbon atoms,
$R^3$ and $R^4$ are each independently a hydrogen atom, an alkyl group having 1-22 carbon atoms or an alkenyl group having 2-22 carbon atoms,
z is an integer of not less than 0,
x and y are each independently an integer of 2-4, or a salt thereof, and
component (B): a cationic surfactant.

[2] The composition of [1], wherein component (A) is a compound of the aforementioned formula (1) wherein z is an integer of 0-10, or a salt thereof.

[3] The composition of [1] or [2], wherein component (A) is a compound of the aforementioned formula (1) wherein z is 7 or 8, or a salt thereof.

[4] The composition of any of [1]-[3], wherein component (A) is a compound of the aforementioned formula (1) wherein x and y are each 4, or a salt thereof.

[5] The composition of any of [1]-[4], wherein component (A) is a compound of the aforementioned formula (1) wherein $R^1$ and $R^2$ are each independently a straight-chain alkyl group having 5-15 carbon atoms, or a salt thereof.

[6] The composition of any of [1]-[5], wherein component (A) is a compound of the aforementioned formula (1) wherein $R^3$ and $R^4$ are each a hydrogen atom, or a salt thereof.

[7] The composition of any of [1]-[5], wherein component (A) is a compound of the aforementioned formula (1) wherein $R^1$ and $R^2$ are each independently a straight-chain alkyl group having 5-15 carbon atoms, $R^3$ and $R^4$ are each a hydrogen atom, z is an integer of 0-10, and x and y are each 4, or a salt thereof.

[8] The composition of any of [1]-[5], wherein component (A) is a compound of the aforementioned formula (1) wherein $R^1$ and $R^2$ are each a straight-chain alkyl group having 5-15 carbon atoms, $R^3$ and $R^4$ are each a hydrogen atom, z is 7 or 8, and x and y are each 4, or a salt thereof.

[9] The composition of any of [1]-[5], wherein component (A) is a compound selected from bis($N^\varepsilon$-lauroyl-L-lysine) sebacoyl amide, and bis($N^\varepsilon$-octanoyl-L-lysine)sebacoyl amide, or a salt thereof.

[10] The composition of any of [1]-[9], wherein component (B) is at least one kind of cationic surfactant selected from the group consisting of quaternary ammonium salt and tertiary amine.

[11] The composition of [10], wherein the quaternary ammonium salt is at least one kind selected from the group consisting of cetyltrimethylammonium chloride, stearyltrimethylammonium chloride, behenyltrimethylammonium chloride and quaternium-87.

[12] The composition of [10], wherein the tertiary amine is at least one kind selected from the group consisting of stearamidopropyl dimethylamine and behenamidopropyl dimethylamine.

[13] The composition of any of [1]-[12], further comprising component (C): a higher alcohol.

[14] The composition of any of [1]-[13], wherein component (A) is contained in a proportion of 0.005-20 wt % relative to the total amount of the composition.

[15] The composition of any of [1]-[14], wherein component (B) is contained in a proportion of 0.005-10 wt % relative to the total amount of the composition.

[16] A hair cosmetic comprising the composition of any of [1]-[15].

Effect of the Invention

According to the present invention, a composition superior in the usability during rinsing, which makes the hair surface after treatment smooth and free of dry feeling, provides a uniform touch feeling from the root of the hair to the tip thereof, and can be utilized as an aqueous cosmetic, can be provided.

According to the present invention, a hair cosmetic which increases hydrophobicity of the hair, decreases cuticle damage and can lead to healthy hair can be provided.

DETAILED DESCRIPTION OF THE PREFERRED EMBODIMENTS

The composition of the present invention is characterized in that it is a composition containing component (A): a compound represented by the formula (1)

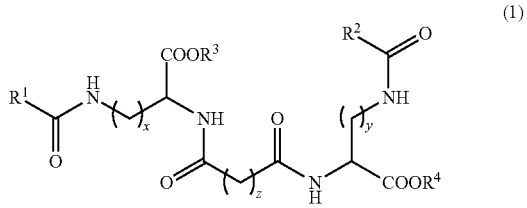

wherein
$R^1$ and $R^2$ are each independently an alkyl group having 5-21 carbon atoms or an alkenyl group having 5-21 carbon atoms,
$R^3$ and $R^4$ are each independently a hydrogen atom, an alkyl group having 1-22 carbon atoms or an alkenyl group having 2-22 carbon atoms,
z is an integer of not less than 0,
x and y are each independently an integer of 2-4, or a salt thereof, and
component (B): a cationic surfactant.

In addition, the composition of the present invention is characterized in that it is a composition further containing component (C): a higher alcohol, in addition to component (A), and component (B).

The embodiment of the present invention is described in detail in the following.

1. Component (A): A Compound Represented by the Formula (1) (Compound (1)) or a Salt Thereof $R^1$ and $R^2$ are each independently an alkyl group having 5-21 carbon atoms or an alkenyl group having 5-21 carbon atoms.

The alkyl group having 5-21 carbon atoms means a straight-chain or branched-chain alkyl group having 5-21 carbon atoms. Specific examples thereof include pentyl group, isopentyl group, neopentyl group, a hexyl group, isohexyl group, neohexyl group, heptyl group, isoheptyl group, neoheptyl group, octyl group, isooctyl group, nonyl group, isononyl group, decyl group, isodecyl group, undecyl group, dodecyl group, tridecyl group, tetradecyl group, pentadecyl group, hexadecyl group, heptadecyl group, octadecyl group, nonadecyl group, icosyl group and the like.

The alkenyl group having 5-21 carbon atoms means a straight-chain or branched-chain alkenyl group having 5-21 carbon atoms. Specific examples thereof include pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group and the like.

An alkyl group having 5-15 carbon atoms means a straight-chain or branched-chain alkyl group having 5-15 carbon atoms. Specific examples thereof include pentyl group, a hexyl group, heptyl group, octyl group, nonyl group, decyl group, undecyl group, dodecyl group, tridecyl group, tetradecyl group, pentadecyl group and the like.

An alkyl group having 7-11 carbon atoms means a straight-chain or branched-chain alkyl group having 7-11 carbon atoms. Specific examples thereof include heptyl group, octyl group, nonyl group, decyl group, undecyl group and the like.

$R^1$ and $R^2$ are preferably each independently an alkyl group having 5-15 carbon atoms, more preferably each independently an alkyl group having 7-11 carbon atoms.

Preferably, $R^1$ and $R^2$ are each a straight chain alkyl group. Furthermore, $R^1$ and $R^2$ are preferably the same.

$R^3$ and $R^4$ are each independently a hydrogen atom, an alkyl group having 1-22 carbon atoms or an alkenyl group having 2-22 carbon atoms.

An alkyl group having 1-22 carbon atoms means a straight-chain or branched-chain alkyl group having 1-22 carbon atoms. Specific examples thereof include methyl group, an ethyl group, a propyl group, an isopropyl group, a butyl group, an isobutyl group, a sec-butyl group, a tert-butyl group, a pentyl group, isopentyl group, neopentyl group, a hexyl group, isohexyl group, neohexyl group, heptyl group, isoheptyl group, neoheptyl group, octyl group, isooctyl group, nonyl group, isononyl group, decyl group, isodecyl group, undecyl group, dodecyl group, tridecyl group, tetradecyl group, pentadecyl group, hexadecyl group, heptadecyl group, octadecyl group, nonadecyl group, icosyl group and the like.

An alkenyl group having 2-22 carbon atoms means a straight-chain or branched-chain alkenyl group having 2-22 carbon atoms. Specific examples thereof include ethenyl group, 1-propenyl group, 2-propenyl group, 1-butenyl group, 2-butenyl group, 3-butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group and the like.

Preferably, both $R^3$ and $R^4$ are hydrogen atoms.

z is an integer of not less than 0.

z is preferably an integer of 0-10, more preferably 7 or 8.

x and y are each independently an integer of 2-4.

x and y are each preferably 4.

As a compound represented by the formula (1), the following compounds can be preferably recited.

(Compound A)

A compound wherein $R^1$ and $R^2$ are each independently a straight-chain alkyl group having 5-15 carbon atoms, $R^3$ and $R^4$ are each a hydrogen atom, z is an integer of 0-10, and x and y are each 4.

(Compound B)

A compound wherein $R^1$ and $R^2$ are each a straight chain alkyl group having 5-15 carbon atoms, $R^3$ and $R^4$ are each a hydrogen atom, z is 7 or 8, and x and y are each 4.

(Compound C)

A compound wherein $R^1$ and $R^2$ are each a straight chain alkyl group having 7-11 carbon atoms, $R^3$ and $R^4$ are each a hydrogen atom, z is 7 or 8, and x and y are each 4.

Specific examples of the compound represented by the formula (1) include bis($N^\varepsilon$-lauroyl-L-lysine)sebacoyl amide, bis($N^\varepsilon$-octanoyl-L-lysine)sebacoyl amide, and a salt thereof.

The salt of the compound represented by the formula (1) is not particularly limited. Examples thereof include alkali metal salts such as sodium salt, potassium salt and the like, alkaline earth metal salts such as calcium salt, magnesium salt and the like, inorganic salts such as aluminum salt, salt with zinc and the like, and organic salts such as organic amine salts such as ammonium salt, monoethanolamine salt, diethanolamine salt, triethanolamine salt and the like, basic amino acid salts such as arginine salt, lysine salt and the like, and the like. One kind of these may be used, or two or more kinds selected from the above-mentioned group may be used in a mixture. From the aspects of easy availability, handling property and the like, alkali metal salt, organic amine salt, or basic amino acid salt is preferable, and sodium salt and potassium salt are particularly preferable.

Compound (1) can be produced by a method known per se or a method analogous thereto (JP-A-2004-323505, Org. Biomol. Chem., 2003, 1, 4124-4131, New J. Chem., 2005, 29, 1439-1444 etc.). For example, as shown in the following formula, of compounds (1), symmetrical compound (1') can be produced by reacting $N^\omega$-acyl amino acid (2) and dicarboxylic acid dichloride (3) in an appropriate solvent.

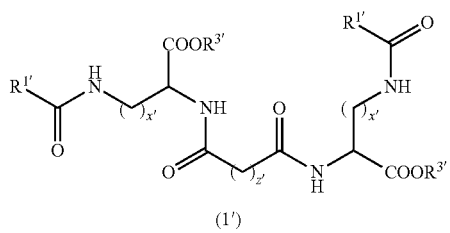

(1')

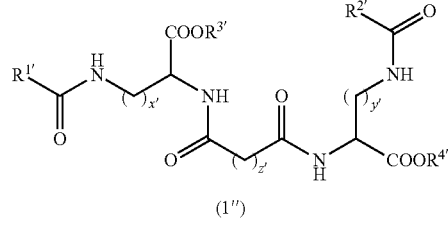

(1")

wherein $R^{1'}$ is an alkyl group having 5-21 carbon atoms or an alkenyl group having 5-21 carbon atoms, $R^{3'}$ is a hydrogen atom, an alkyl group having 1-22 carbon atoms or an alkenyl group having 2-22 carbon atoms, z' is an integer of not less than 0, and x' is an integer of 2-4.

Examples of the $N^\omega$-acyl amino acid (2) include $N^\varepsilon$-acyl lysine (e.g., $N^\varepsilon$-hexanoyl-L-lysine, $N^\varepsilon$-octanoyl-L-lysine etc.), $N^\delta$-acyl ornithine (e.g., $N^\delta$-hexanoyl-L-ornithine etc.), $N^\gamma$-acyl-α,γ-diaminobutyric acid and the like.

Examples of the dicarboxylic acid dichloride (3) include oxalyl chloride, malonyl chloride, succinyl chloride, glutaryl chloride, adipoyl chloride, pimeloyl chloride, suberoyl chloride, azelaoyl chloride, sebacoyl chloride, dodecanedioyl chloride and the like. The amount of dicarboxylic acid dichloride (3) to be used is generally 0.4-0.6 equivalent relative to $N^\omega$-acyl amino acid (2).

While the solvent is not particularly limited as long as it is inert to the reaction, examples thereof include ethers such as diethyl ether, tetrahydrofuran and the like.

In addition, of compounds (1), asymmetric compound (1") can be produced as follows. First, $N^\omega$-acyl amino acid (2) and dicarboxylic acid monochloride monoester (4) are reacted in an appropriate solvent to give compound (5) (step 1). Then, the primary ester moiety of the obtained compound (5) is hydrolyzed in the presence of a base such as sodium hydroxide, potassium hydroxide and the like, the carboxylic acid moiety is chlorinated with a chlorinating agent such as thionyl chloride and the like, and the compound is reacted with $N^\omega$-acyl amino acid (2') which is different from $N^\omega$-acyl amino acid (2) used in the aforementioned step 1 (step 2), whereby derivative (1") can be produced.

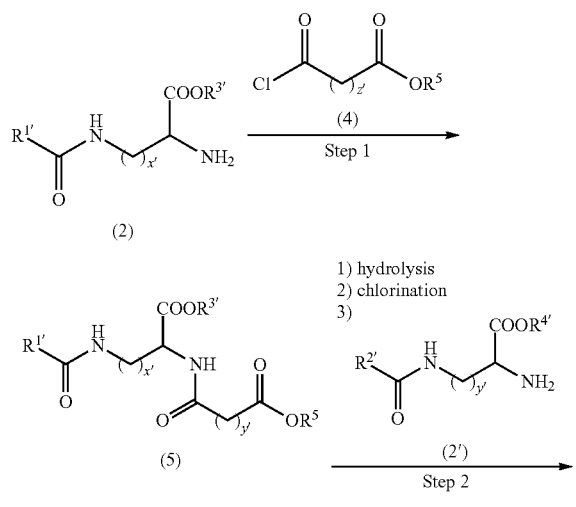

wherein $R^{1'}$, $R^{3'}$, z' and x' are as defined above, $R^{2'}$ is an alkyl group having 5-21 carbon atoms or an alkenyl group having 5-21 carbon atoms, $R^{4'}$ is a hydrogen atom, an alkyl group having 1-22 carbon atoms or an alkenyl group having 2-22 carbon atoms, $R^5$ is an alkyl group such as a methyl group, an ethyl group and the like, and y' is an integer of 2-4.

As Nω-acyl amino acids (2) and (2'), $N^\omega$-acyl amino acids similar to those mentioned above can be used.

As dicarboxylic acid monochloride monoester (4), a commercially available product can be used as is when it is commercially available, or one produced by a method known per se or a method analogous thereto can also be used.

Compound (1) obtained by the aforementioned method can be converted to a salt of compound (1) by a reaction with alkali metal hydroxide such as sodium hydroxide, potassium hydroxide and the like, alkali earth metal hydroxide such as calcium hydroxide and the like, organic amine base, or the like.

The content of component (A): compound (1) or a salt thereof in the composition of the present invention is generally 0.005-20 wt %, preferably 0.01-10 wt %, more preferably 0.01-5.0 wt %, further preferably 0.02-2.5 wt %, relative to the total amount of the composition.

2. Component (B): Cationic Surfactant

Examples of the "cationic surfactant" in the present specification include quaternary ammonium salt, tertiary amine and the like.

Specific examples of the quaternary ammonium salt include monoalkyl quaternary ammonium salts (e.g., lauryltrimethylammonium chloride, cetyltrimethylammonium chloride, stearyltrimethylammonium chloride (steartrimonium chloride), behenyltrimethylammonium chloride (behentrimonium chloride), cetyltrimethylammonium bromide, stearyltrimethylammonium bromide, dipolyoxyethylene oleylmethylammonium chloride, polyoxyethylene behenyltrimethylammonium chloride, methylsulfuric acid behenyltrimethylammonium, stearylhydroxypropyl trimethylammonium, dipolyoxyethylene oleylmethylammonium chloride, cetrimonium saccharinate, stearyldimethylbenzylammonium chloride, quaternium-33 etc.), monoalkoxy quaternary ammonium salts (e.g., octadecyoxy propyl trimethylammonium chloride etc.), dialkyl type quaternary ammonium salts (e.g., distearyldimethylammonium chloride, dicocoyldimethylammonium chloride, dialkyl(C12-C18)dimethylammonium chloride, dioleyldimethylammonium chloride, lanolin fatty acid aminopropyl ethyldimethyl ammonium ethyl sulfate, distearoylethylhydroxyethylammonium methylsulfate, dicocoyldimethylammonium chloride, coconut oil alkyl PG dimonium chloride acid, linoleamidopropyl PG dimonium chloride phosphate, etc.), cyclic quaternary ammonium salts (e.g., alkyldimethylbenzylammonium chloride, lauryl pyridinium chloride, alkyldimethyl(ethylbenzyl)ammonium chloride, quaternium-87 etc.) and the like can be mentioned.

Preferable examples of the quaternary ammonium salt include cetyltrimethylammonium chloride, stearyltrimethylammonium chloride, behenyltrimethylammonium chloride, quaternium-87 and the like.

Specific examples of the tertiary amine include alkylamideamine tertiary amines (e.g., stearamido propyl dimethylamine, behenamidopropyl dimethylamine, stearamidopropyldiethylamine etc.), alkylamine tertiary amines (e.g., dimethylstearamide, behenyl dimethylamine, POE coconut oil alkylamine, POE oleyl amine, POE stearylamine etc.), alkylalkanolamine tertiary amines (e.g., polypropylene glycol/polyethylene glycol stearylamine etc.) and the like.

Preferable examples of the tertiary amine include stearamidopropyl dimethylamine, behenamidopropyl dimethylamine and the like.

The cationic surfactant may be used alone or two or more kinds thereof may be used in a mixture.

The content of component (B): cationic surfactant in the composition of the present invention is generally 0.005-10 wt %, preferably 0.05-8.0 wt %, relative to the total amount of the composition.

3. Component (C): Higher Alcohol

The "higher alcohol" in the present specification is preferably a straight-chain alcohol having 12-22 carbon atoms or branched-chain alcohol having 12-30 carbon atoms. Specific examples of the "higher alcohol" include straight chain alcohol having 12-22 carbon atoms (e.g., lauryl alcohol, myristyl alcohol, cetanol, stearyl alcohol, behenyl alcohol, oleyl alcohol, cetostearyl alcohol, hydrogenated rapeseed oil alcohol etc.), branched-chain alcohol having 12-30 carbon atoms (e.g., monostearyl glycerol ether(batyl alcohol), 2-decyltetradecynol, lanolin alcohol, cholesterol, phytosterol, hexyldodecanol, hexyldecanol, isostearyl alcohol, octyldodecanol etc.).

Preferable examples of the "higher alcohol" include a straight-chain alcohol having 12-22 carbon atoms, and stearyl alcohol, behenyl alcohol, oleyl alcohol, cetostearyl alcohol, cetanol and the like are more preferable.

The content of component (C): higher alcohol in the composition of the present invention is generally 0.01-20 wt %, preferably 0.1-15 wt %, relative to the total amount of the composition.

The present invention also relates to a hair cosmetic containing the aforementioned composition of the present invention.

While the hair cosmetic of the present invention is not particularly limited, specifically, permanent agent, hair dyeing agent, hair-growth medicine, hair-growth drug, hair cream, hair lotion, hair toner, hair milky lotion, hair ointment, hair treatment, conditioner, shampoo, rinse and the like can be mentioned.

The hair cosmetic of the present invention may contain components that can be generally added to a cosmetic for hair, as long as the effect of the present invention is not inhibited. Specific examples include oil, chelating agent, amino acids, polyvalent alcohol, polyamino acid and salt thereof, water-soluble polymer, sugar alcohol and alkylene oxide adduct thereof, lower alcohol, animal and plant extract, nucleic acid, vitamin, enzyme, anti-inflammatory agent, antimicrobial agent, preservative, antioxidant, ultraviolet absorber, adiaphoretic, pigment, dye, oxidation dye, pH adjuster, pearly sheen agent, wetting agent and the like.

The composition of the present invention, and a hair cosmetic containing the composition can be produced according to a conventional method.

Other features of the invention will become apparent in the course of the following descriptions of exemplary embodiments which are given for illustration of the invention and are not intended to be limiting thereof.

EXAMPLES

The present invention is concretely explained in the following by referring to Production Example and Examples. The present invention is not limited by the following Production Example and Examples. Unless particularly indicated, "%" means "wt %".

Production Example 1

Synthesis of bis($N^\varepsilon$-lauroyl-L-lysine)sebacoylamide disodium salt $N^\varepsilon$-lauroyl-L-lysine (8.2 g, 25 mmol) was dissolved in water (70 g) and 25% aqueous sodium hydroxide solution (10 g), and diethyl ether (80 g) was added. Sebacoyl chloride (3.3 g, 14 mmol) was slowly added to the ether layer. The two-layer solution was stirred for about 1 hr while maintaining at 0° C., and then at room temperature for 23 hr. Then, 75% sulfuric acid was added dropwise to adjust to pH 2, the obtained white precipitate was collected by filtration, washed well with water and dried. The obtained compound was dissolved in an aqueous sodium hydroxide solution to give a 10% aqueous bis($N^\varepsilon$-lauroyl-L-lysine)sebacoyl amide disodium salt solution.

Production Example 2

Synthesis of bis($N^\varepsilon$-octanoyl-L-lysine)sebacoylamide disodium salt $N^\varepsilon$-octanoyl-L-lysine (6.8 g, 25 mmol) was dissolved in water (70 g) and 25% aqueous sodium hydroxide solution (10 g), and diethyl ether (80 g) was added. Sebacoyl chloride (3.3 g, 14 mmol) was slowly added to the ether layer. The two-layer solution was stirred for about 1 hr while maintaining at 0° C., and then at room temperature for 23 hr. Then, 75% sulfuric acid was added dropwise to adjust to pH 2, the obtained white precipitate was collected by filtration, washed well with water and dried. The obtained compound was dissolved in an aqueous sodium hydroxide solution to give a 10% aqueous bis($N^\varepsilon$-octanoyl-L-lysine)sebacoyl amide disodium salt solution.

1H-NMR of bis($N^\varepsilon$-octanoyl-L-lysine)sebacoyl amide (free form)

1H-NMR (400 MHz, DMSO-d6, TMS, 25° C.): δ0.85 (t, J=6.8 Hz, 6H), 1.20-1.29 (m, 28H), 1.32-1.38 (m, 4H), 1.45-1.50 (m, 8H), 1.54-1.59 (m, 4H), 2.02 (t, J=7.4 Hz, 4H), 2.09 (t, J=7.4 Hz, 4H), 2.99 (q, J=6.5 Hz, 4H), 4.08-4.47 (m, 2H), 7.73 (t, J=5.6 Hz, 2H), 7.97 (d, J=8.0 Hz, 2H).

[Examples 1-7] [Comparative Examples 1-4]

Preparation and Evaluation of Hair Cosmetic

Preparation of Hair Cosmetics of Examples 1-7 and Comparative Examples 1, 2

The components of (I) described in the following Table 1 were mixed, heated to 80-85° C. and dissolved by stirring. This mixture was mixed with the components of (II) described in the following Table 1, which had been heated to 80-85° C. and dissolved by stirring in advance, and the mixture was emulsified by a homomixer at 80° C., and cooled with stirring. Thereafter, the mixture was adjusted to pH 3.9±0.1 in Examples 1-4 and Comparative Example 1 and adjusted to pH 5.3 by using an aqueous sodium hydroxide solution as necessary in Examples 5-7 and Comparative Example 2. The prepared hair cosmetics were preserved at room temperature.

Preparation of Hair Cosmetics of Comparative Examples 3, 4

The components of (II) described in the following Table 1 were mixed, heated to 80-85° C. and dissolved by stirring. To this mixture was added a mixture of the components of (III) described in the following Table 1 and an aqueous sodium hydroxide solution, which had been dissolved by stirring in advance, and the precipitated $N^\varepsilon$-lauroyllysine was dispersed. Furthermore, this mixture was mixed with the components of (I) described in the following Table 1, which had been heated to 80-85° C. and dissolved by stirring in advance, and the mixture was emulsified by a homomixer at 80° C., and cooled with stirring. Thereafter, the mixture was adjusted to pH 3.9±0.1 in Comparative Example 3 and adjusted to pH 5.3 by using citric acid and an aqueous sodium hydroxide solution as necessary in Comparative Example 4. The prepared hair cosmetics were preserved at room temperature.

For the evaluation of the sense of use and texture in the following evaluations 1-6, a plurality of bundles of natural hair (European Medium Brown Hair, De Meo Brothers/NY, length 30 cm, weight 10 g) were prepared, and five test subjects performed treatment and evaluation by the following methods.

Evaluations 1, 2: Absence of Sliminess During Rinsing and Fast Rinsing Off

The above-mentioned hair bundles were washed twice with 15% sodium laureth sulfate (SLES), and a hair cosmetic (2 g) prepared as mentioned above was applied thereon. After the cosmetic was sufficiently applied on the whole hair, it was rinsed off with tap water at 35-40° C., and the sense of use was evaluated. The test subjects were made to recognize the sense of use during rinsing in Comparative Examples 1 and 2, and evaluated Examples 1-4 and Comparative Example 3 with Comparative Example 1 as the standard and Examples 5-7 and Comparative Example 4 with Comparative Example 2 as the standard, and according to the following criteria.
6 points: very good
5 points: good
4 points: a little good
3 points: normal, not different from standard
2 points: a little bad
1 point: bad
0 point: very bad The average of the test subjects was calculated and evaluated according to the following criteria.
⊙: average not less than 5.0
○: average not less than 4.0 and less than 5.0
Δ: average not less than 3.0 and less than 4.0
x: average less than 3.0

Evaluations 3-6: Evaluation of Smoothness, Absence of Dryness, Uniform Touch Feeling, Less Kinkiness (Gathering of Hair Tips) of Hair Surface After Drying The above-mentioned hair bundles were washed twice with 15% sodium laureth sulfate (SLES), and a hair cosmetic (2 g) prepared as mentioned above was applied thereon. After the cosmetic was sufficiently applied on the whole hair, it was rinsed off with tap water at 35-40° C. for 30 sec. Water was drained and the hair was dried with towel. The hair was air dried as it was, and the hair after drying was evaluated. For evaluation, the hair was compared with the hair bundle before treatment with the hair cosmetic, and scored according to the following criteria.
6 points: very good
5 points: good
4 points: a little good
3 points: normal, not different from standard
2 points: a little bad
1 point: bad
0 point: very bad The average of the test subjects was calculated and evaluated according to the following criteria.
⊙: average not less than 5.0
○: average not less than 4.0 and less than 5.0
Δ: average not less than 3.0 and less than 4.0
x: average less than 3.0

For the physical property evaluation in the following evaluations 7 and 8, a plurality of hair bundles (length 15 cm, weight 1 g) were prepared and used. The hair cosmetics of Examples 2 and 4 and Comparative Examples 1 and 3 (each 0.5 g) prepared as mentioned above were applied to the hair bundle, thereafter rinsed off by immersing in tap water (100 mL) at 35-40° C. The hair bundle was repeatedly washed 5 times, water was drained and the hair was air dried as it was, and the following evaluation was performed the next day.

Evaluation 7: Hydrophobicity of Hair (Contact Angle Measurement)

For evaluation of the hydrophobicity of hair, the contact angle was measured as follows. Water (1.2 μL) was set within 8 cm from the hair tip of the above-mentioned hair bundle, and water drop was photographed 20 sec later by a microscope. With an average of the right and left angles of water drop and hair as values of one time, the measurement was performed 6 times, and the average thereof was determined to be a contact angle value. From the contact angle before treatment with the hair cosmetic and the contact angle after the hair cosmetic treatment, the change rate (%) was calculated according to the following formula. The larger the change rate of the contact angle is, the higher the hydrophobicity of the hair is, which indicates that the hair tip ends which had great damage became close to those of healthy hair by the hair cosmetic.

$$\text{contact angle change rate (\%)}=100\times(1-\text{contact angle after treatment/contact angle before treatment})$$

The contact angle change rate was evaluated by the following criteria.
⊙: contact angle change rate of not less than 20%
○: contact angle change rate of not less than 15% and less than 20%
Δ: contact angle change rate of not less than 10% and less than 15%
x: contact angle change rate of less than 10%

Evaluation 8: Slipperiness Test (MIU Rate)

The above-mentioned hair bundles were fixed on the main body of a friction tester (manufactured by Kato tech, KES-SE(STP)) in a constant-temperature and humidity chamber (23° C., 40% R.H.), a load of 25 g was applied, and the average frictional coefficient (MIU) was measured using a fingerprint-type silicone resin as a friction block. The friction tester was moved to the hair tip direction of the hair bundle at a rate of 0.1 cm/sec and MIU was obtained. The measurement was performed twice, and the average was taken as MIU of the hair after hair cosmetic treatment. From the MIU before treatment with the hair cosmetic and the MIU after the hair cosmetic treatment, the MIU rate (%) was calculated according to the following formula. The larger the MIU rate is, the more improved the slip property of the hair surface is, which indicates that the dryness are reduced.

$$MIU \text{ rate } (\%) = 100 \times (1 - MIU \text{ after treatment}/MIU \text{ before treatment})$$

The MIU rate was evaluated by the following criteria.
⊙: MIU rate of not less than 40%
○: MIU rate of not less than 35% and less than 40%
Δ: MIU rate of not less than 30% and less than 35%
x: MIU rate of less than 30%
The results are shown in Table 1.

function evaluation that the smoothness and slipperiness were improved, and dryness were reduced, as compared to the hair before treatment.

Furthermore, the cosmetics of Examples 2 and 4 of the present invention increased the hydrophobicity of the hair tips, which indicates that the hair tips became closer to those of healthy hair. This means that the difference between the root with a small damage and the hair tips with a large damage became small, and supported the function evaluation of "uniform touch feeling".

INDUSTRIAL APPLICABILITY

The present invention can provide a composition superior in the usability during rinsing, which makes the hair surface

TABLE 1

|  |  |  | Example | | | | | | | Comparative Example | | | |
| --- | --- | --- | --- | --- | --- | --- | --- | --- | --- | --- | --- | --- | --- |
|  |  |  | 1 | 2 | 3 | 4 | 5 | 6 | 7 | 1 | 2 | 3 | 4 |
| component (A) | component (II) | Production Example 1 (as 10% solution) | 0.50 | 3.00 | 10.00 | — | 0.50 | 3.00 |  | — | — | — |  |
|  |  | Production Example 2 (as 10% solution) | — | — | — | 3.00 | — | — | 3.00 | — | — | — |  |
|  | component (III) | N$^\varepsilon$-lauroyllysine | — | — | — | — | — | — | — | — | — | 0.30 | 0.05 |
| component (B) | component (I) | steartrimonium chloride | — | — | — | — | 2.00 | 2.00 | 2.00 | — | 2.00 | — | 2.00 |
|  |  | behentrimonium chloride | 1.30 | 1.30 | 1.30 | 1.30 | — | — | — | 1.30 | — | 1.30 | — |
|  | component (II) | Stearamidopropyl dimethylamine | 0.20 | 0.20 | 0.20 | 0.20 | — | — | — | 0.20 | — | 0.20 | — |
| component (C) | component (I) | cetanol | 6.00 | 6.00 | 6.00 | 6.00 | — | — | — | 6.00 | — | 6.00 | — |
|  |  | cetostearyl alcohol | — | — | — | — | 4.00 | 4.00 | 4.00 | — | 4.00 | — | 4.00 |
|  | component (II) | water | balance | balance | balance | balance | balance | balance | balance | balance | balance | balance | balance |
| preservative |  | sodium benzoate | 0.20 | 0.20 | 0.20 | 0.20 | 0.20 | 0.20 | 0.20 | 0.20 | 0.20 | 0.20 | 0.20 |
|  |  | methylparaben | 0.20 | 0.20 | 0.20 | 0.20 | 0.20 | 0.20 | 0.20 | 0.20 | 0.20 | 0.20 | 0.20 |
| pH adjuster |  | glutamic acid | 1.10 | 1.10 | 1.10 | 1.10 | — | — | — | 1.10 | — | 1.10 | — |
|  |  | lactic acid | — | — | — | — | 0.10 | 0.10 | 0.10 | — | 0.10 | — | 0.10 |
|  |  | citric acid | — | — | — | — | — | — | — | — | — | q.s. | q.s. |
|  |  | sodium hydroxide | — | — | — | — | q.s. | — | — | — | q.s. | q.s. | q.s. |
| Evaluation 1 |  | absence of sliminess | ⊙ | ⊙ | ⊙ | ○ | ○ | ○ | ○ | standard | standard | X | X |
| Evaluation 2 |  | fast rinsing off | ⊙ | ⊙ | ⊙ | ○ | ○ | ○ | ○ | standard | standard | X | X |
| Evaluation 3 |  | smoothness of surface | ⊙ | ⊙ | ⊙ | ⊙ | ⊙ | ⊙ | ⊙ | X | X | Δ | Δ |
| Evaluation 4 |  | absence of dryness | ⊙ | ⊙ | ○ | ⊙ | ⊙ | ⊙ | ⊙ | X | X | X | X |
| Evaluation 5 |  | uniform touch feeling | ⊙ | ⊙ | ⊙ | ⊙ | ⊙ | ⊙ | ⊙ | X | X | Δ | X |
| Evaluation 6 |  | less kinky (gathering of hair tips) | ⊙ | ⊙ | ⊙ | ○ | ⊙ | ⊙ | ⊙ | X | X | ○ | X |
| Evaluation 7 |  | hydrophobicity of hair (contact angle measurement) | — | ⊙ | — | ⊙ | — | — | — | X | — | X | — |
| Evaluation 8 |  | slipperiness test (MIU rate) | — | ⊙ | — | — | — | — | — | Δ | — | Δ | — |

The cosmetics of Examples 1-7 of the present invention added with component (A) showed no sliminess during rinsing and was rinsed off rapidly, as compared to the hair cosmetics of Comparative Examples 1, 2 without addition of component (A).

The hair treated with the cosmetics of Examples 1-7 of the present invention had a smooth surface, was free of dry feeling, had a uniform touch feeling up to the hair tip, was less kinky hair fiber in appearance, and was superior in the gathering of hair tips, as compared to the hair treated with the cosmetics of Comparative Examples 1, 2 without addition of component (A) or the cosmetics of Comparative Examples 3, 4 added with N$^\varepsilon$-lauroyllysine instead of component (A).

In addition, the high MIU rate shown by the cosmetic of Example 2 of the present invention supported the results of after treatment smooth and free of dry feeling, provides a uniform touch feeling from the root of the hair to the tip thereof, and can be utilized as an aqueous cosmetic.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A composition, comprising:
   (A) at least one compound selected from the group consisting of bis($N^\varepsilon$-lauroyl-L-lysine)sebacoyl amide disodium salt and bis($N^\varepsilon$-octanoyl-L-lysine)sebacoyl amide disodium salt; and
   (B) at least one cationic surfactant selected from the group consisting of a quaternary ammonium salt and a tertiary amine,
   wherein said quaternary ammonium salt is at least one kind selected from the group consisting of cetyltrimethylammonium chloride, stearyltrimethylammonium chloride, behenyltrimethylammonium chloride, and quaternium-87, and
   wherein said tertiary amine is at least one kind selected from the group consisting of stearamidopropyl dimethylamine and behenamidopropyl dimethylamine.

2. The composition according to claim 1, which comprises bis($N^\varepsilon$-lauroyl-L-lysine)sebacoyl amide disodium salt.

3. The composition according to claim 1, which comprises bis($N^\varepsilon$-octanoyl-L-lysine)sebacoyl amide disodium salt.

4. A hair cosmetic, comprising a composition according to claim 1.

5. The composition according to claim 1, further comprising:
   (C) at least one higher alcohol selected from the group consisting of a straight-chain alcohol having 12 to 22 carbon atoms, a branched-chain alcohol having 12 to 30 carbon atoms, and mixtures thereof.

6. A hair cosmetic, comprising a composition according to claim 5.

7. The composition according to claim 5, which comprises bis($N^\varepsilon$-lauroyl-L-lysine)sebacoyl amide disodium salt.

8. The composition according to claim 5, which comprises bis($N^\varepsilon$-octanoyl-L-lysine)sebacoyl amide disodium salt.

9. The composition according to claim 1, wherein said (A) is present in a proportion of 0.005 to 20 wt % relative to the total weight of said composition.

10. A hair cosmetic, comprising a composition according to claim 9.

11. The composition according to claim 9, which comprises bis($N^\varepsilon$-lauroyl-L-lysine)sebacoyl amide disodium salt.

12. The composition according to claim 9, which comprises bis($N^\varepsilon$-octanoyl-L-lysine)sebacoyl amide disodium salt.

13. The composition according to claim 1, wherein said (B) is present in a proportion of 0.005 to 10 wt % relative to the total weight of said composition.

14. A hair cosmetic, comprising a composition according to claim 13.

15. The composition according to claim 13, which comprises bis($N^\varepsilon$-lauroyl-L-lysine)sebacoyl amide disodium salt.

16. The composition according to claim 13, which comprises bis($N^\varepsilon$-octanoyl-L-lysine)sebacoyl amide disodium salt.

* * * * *